(12) United States Patent
Scalo et al.

(10) Patent No.: US 11,506,783 B2
(45) Date of Patent: Nov. 22, 2022

(54) METHOD OF PROCESSING AN IMAGE

(71) Applicant: Purdue Research Foundation, West Lafayette, IN (US)

(72) Inventors: Carlo Scalo, Lafayette, IN (US); Pavlos P Vlachos, West Lafayette, IN (US); Brett A Meyers, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 842 days.

(21) Appl. No.: 16/291,157

(22) Filed: Mar. 4, 2019

(65) Prior Publication Data
US 2019/0277965 A1 Sep. 12, 2019

Related U.S. Application Data

(60) Provisional application No. 62/640,849, filed on Mar. 9, 2018.

(51) Int. Cl.
*G01S 15/89* (2006.01)
*A61B 8/00* (2006.01)
(Continued)

(52) U.S. Cl.
CPC ............ *G01S 15/89* (2013.01); *A61B 5/0033* (2013.01); *A61B 8/06* (2013.01); *A61B 8/461* (2013.01); *A61B 8/488* (2013.01); *A61B 8/5207* (2013.01)

(58) Field of Classification Search
CPC ....... A61B 5/0033; A61B 8/06; A61B 8/0883; A61B 8/461; A61B 8/488; A61B 8/5207;
(Continued)

(56) References Cited

U.S. PATENT DOCUMENTS

| 5,947,903 A | 9/1999 | Ohtsuki et al. |
| 7,270,635 B2 | 9/2007 | Pedrizzetti et al. |

(Continued)

FOREIGN PATENT DOCUMENTS

EP 0890825 A1 1/1999

OTHER PUBLICATIONS

Jensen et al.: Ultrasound Vector Flow Imaging—Part I: Sequential Systems, 2016 (Year: 2016).*
(Continued)

*Primary Examiner* — Mekonen T Bekele
(74) *Attorney, Agent, or Firm* — Purdue Research Foundation

(57) ABSTRACT

A non-transitory computer-readable medium encoded with a computer-readable program, which, when executed by a processor, will cause a computer to execute a method of processing an image, wherein the method includes receiving a 2-D color Doppler image. The method additionally includes extracting a single component velocity field of a 2-D plane from the 2-D color Doppler image. Further, the method includes receiving a geometrical boundary of a region of interest within the 2-D color Doppler image. Moreover, the method includes applying a plurality of boundary conditions to the geometrical boundary, an at least one inlet, and an at least one outlet, of the single component velocity field of a 2-D plane. The method additionally includes solving a streamfunction vorticity formulation to reconstruct a transverse velocity component. Further, the method includes outputting a reconstructed 2-D 2-component velocity based on the transverse velocity component.

20 Claims, 3 Drawing Sheets

(51) Int. Cl.
  *A61B 8/08* (2006.01)
  *A61B 8/06* (2006.01)
  *A61B 5/00* (2006.01)
(58) Field of Classification Search
  CPC ...... A61B 8/5223; G01S 15/89; G16H 50/30; G16H 30/40
  See application file for complete search history.

(56) References Cited

U.S. PATENT DOCUMENTS

| | | | |
|---|---|---|---|
| 8,858,437 B2* | 10/2014 | Pedrizzetti | G06T 11/206 600/407 |
| 9,267,828 B2 | 2/2016 | Ono et al. | |
| 10,914,826 B2* | 2/2021 | Daigle | G01S 15/8979 |

OTHER PUBLICATIONS

Pavlos P. Vlachos"Colour-Doppler echocardiography flow field velocity reconstruction using a streamfunction-vorticity formulation", 2020 (Year: 2020).*

Jensen et al. Ultrasoundvectorflowimaging—Parti:Sequentialsystems,2016(Year:2016) (Year:2016).*

PavlosP.Vlachos"Colour-Dopplerechocardiographyflowfieldvelocityreconstructionusingastreamfunction-vorticityformulation", 2020(Year:2020) (Year: 2016).*

Garcia, D. et al., "Two-Dimensional Intraventricular Flow Mapping by Digital Processing Conventional Color-Doppler Echocardiography Images," IEEE Transactions on Medical Imaging, vol. 29, No. 10, Oct. 2010, 1701-13.

Laroche, S. et al., "A Variational Analysis Method for Retrieval of Three-Dimensional Wind Field from Single-Doppler Radar Data," Journal of the Atmospheric Sciences, vol. 51, No. 18, 1994, 2664-82.

Liou, Y.-C., "An Explanation of the Wind Speed Underestimation Obtained from a Least Squares Type Single-Doppler Radar Velocity Retrieval Method," Journal of Applied Meteorology, vol. 41, No. 7, Jul. 2002, 811-23.

Xu, Q. et al., "Adjoint-Method Retrievals of Low-Altitude Wind Fields from Single-Doppler Wind Data," Journal of Atmospheric and Oceanic Technology , vol. 11, No. 2, Apr. 1994, 579-85.

* cited by examiner

405 → 410 → 415 → 420 → 425 → 430 → 435 → 440

METHOD OF PROCESSING AN IMAGE

CROSS-REFERENCE TO RELATED APPLICATIONS

The present U.S. Patent Application is related to and claims the priority benefit of U.S. Provisional Patent Application Ser. No. 62/640,849, filed Mar. 9, 2018, the contents of which is hereby incorporated by reference in its entirety into this disclosure.

BACKGROUND

This section introduces aspects that may help facilitate a better understanding of the disclosure. Accordingly, these statements are to be read in this light and are not to be understood as admissions about what is or is not prior art.

Conventional art for Doppler image reconstruction relate to procedures solving solely a continuity equation and require an additional assumption of symmetry. Some conventional procedures attempt to close the problem by decomposing the velocity field formulation into rotational and irrotational components, thereby producing a more generalized formulation. This approach is largely phased out in favor of the methods which present a formulation that solves the continuity equation in a scalar formulation. This formulation allows for a more robust solver, however, boundary conditions for the solver are difficult. Additionally, rotational flow features are under-resolved due to formulation assumptions. Meteorology methods utilize continuity along with momentum equations and allow the field to vary in time to improve initial estimates. Their formulations are solved using least squares methods but largely underestimate the exact velocity.

There is, therefore an unmet need for a novel approach for a new formulation that greatly improves the physical consistency and measurement accuracy. Based on improvements of methods that process a Doppler image, more accurate post-measurement quantities relevant to each field such as pressure, circulation, and energy loss can be obtained.

SUMMARY

Doppler velocity measurement by Doppler image processing is utilized in several fields including meteorology, oceanography, petroleum production, and medical examinations to measure flow velocity of a working fluid. FIG. 1 illustrates measuring flow velocities in medical examinations. As indicated in FIG. 1, such measurements are often rendered as 2 dimensional images.

Various embodiments of the present disclosure relate to a novel image processing approach to reconstruct 2 dimensional (2-D) 2-component or 3 dimensional (3-D) 3-component velocity fields from a single velocity component Doppler velocity image. In one or more embodiments, the above methodology is used to create a velocity vector field image.

One aspect of the present application relates to a non-transitory computer-readable medium encoded with a computer-readable program, which, when executed by a processor, will cause a computer to execute a method of processing an image, wherein the method includes receiving a 2-D color Doppler image. The method additionally includes extracting a single component velocity field of a 2-D plane from the 2-D color Doppler image. Further, the method includes receiving a geometrical boundary of a region of interest within the 2-D color Doppler image. Moreover, the method includes applying a plurality of boundary conditions to the geometrical boundary, with at least one inlet, and at least one outlet, of the single component velocity field of a 2-D plane. The method additionally includes solving a streamfunction-vorticity formulation to reconstruct a transverse velocity component. Further, the method includes outputting a reconstructed 2-D 2-component velocity based on the transverse velocity component.

Another aspect of the present application relates to a non-transitory computer-readable medium encoded with a computer-readable program, which, when executed by a processor, will cause a computer to execute a method of processing an image, wherein the method includes receiving a 2-D color Doppler image. The method additionally includes extracting a single component velocity field of a 2-D plane from the 2-D color Doppler image. Further, the method includes receiving a geometrical boundary of a region of interest within the 2-D color Doppler image. Moreover, the method includes applying a plurality of boundary conditions to the geometrical boundary, an at least one inlet, and an at least one outlet, of the single component velocity field of a 2-D plane. The method additionally includes solving a streamfunction vorticity formulation to reconstruct a transverse velocity component. Further, the method includes outputting a reconstructed 2-D 2-component velocity based on the transverse velocity component. The solving the streamfunction vorticity formulation to reconstruct the transverse velocity component includes initializing a plurality of vorticity values for each point of a flow field of the 2-D color Doppler image within the geometrical boundary of the region of interest. The solving further includes solving, numerically, Poisson Equation for a streamfunction with an iterated vorticity as a source term of the Poisson Equation, thereby generating an updated streamfunction. Next the solving includes calculating a 2-D 2-component velocity field using the updated streamfunction. Further, the solving includes comparing the updated streamfunction with the one determined at the previous iteration to determine whether a difference between the updated stream function and the stream function is above or below a tolerance value.

Still another aspect of the present application relates to a non-transitory computer-readable medium encoded with a computer-readable program, which, when executed by a processor, will cause a computer to execute a method of processing an image, wherein the method includes receiving a 2-D color Doppler image. The method further includes extracting a single component velocity field of a 2-D plane from the 2-D color Doppler image. Next, the method includes receiving a geometrical boundary of a region of interest within the 2-D color Doppler image. Additionally, the method includes applying a plurality of boundary conditions to the geometrical boundary, an at least one inlet, and an at least one outlet, of the single component velocity field of a 2-D plane. Further, the method includes solving a streamfunction-vorticity formulation to reconstruct a transverse velocity component based on the single component velocity field defined on a 2-D plane, wherein the solving the streamfunction includes initializing a plurality of vorticity values for each point of a flow field of the 2-D color Doppler image within the geometrical boundary of the region of interest. The solving the streamfunction includes iterating, by solving numerically, Poisson Equation for the streamfunction with a vorticity as a source term of the Poisson Equation until a difference between a resulting streamfunction and the streamfunction is below a tolerance value. Next, the method of processing the image continues with calculating a 2-D 2-component velocity field using the resulting streamfunction. Further, the method includes reconstructing the transverse velocity component based on the 2-D 2-component velocity field. Moreover, the method includes outputting a reconstructed 2-D 2-component velocity based on the transverse velocity component.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry, various features may not be drawn to scale and are used for illustration purposes only. In fact, the dimensions of the various features in the drawings may be arbitrarily increased or reduced for clarity of discussion.

DETAILED DESCRIPTION

The following disclosure provides many different embodiments, or examples, for implementing different features of the present application. Specific examples of components and arrangements are described below to simplify the present disclosure. These are examples and are not intended to be limiting. The making and using of illustrative embodiments are discussed in detail below. It should be appreciated, however, that the disclosure provides many applicable concepts that can be embodied in a wide variety of specific contexts. In at least some embodiments, one or more embodiment(s) detailed herein and/or variations thereof are combinable with one or more embodiment(s) herein and/or variations thereof.

Figure 1:
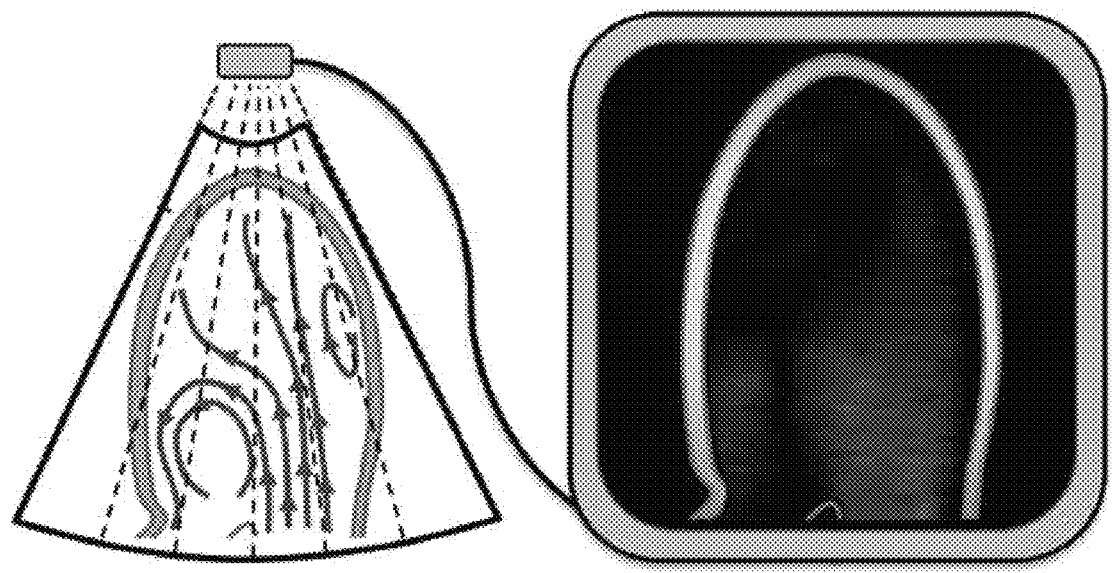
FIG. 1 illustrates measuring flow velocities in medical examinations.
Figure 2:
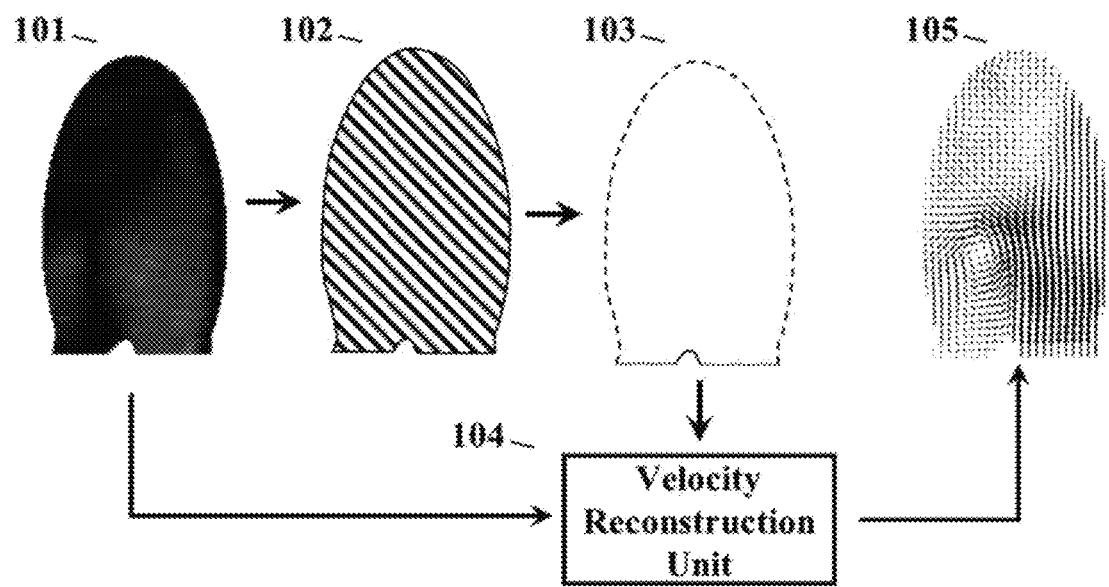
FIG. 2 illustrates velocity reconstruction in accordance with one or more embodiments.

Various embodiments of the present application relate to a novel image processing approach to reconstruct 2-D 2-component or 3-D 3-component velocity fields from a single velocity component Doppler velocity image. The above procedure of processing a Doppler image results in more accurate measurement quantities such as pressure, circulation, and energy loss. FIG. 2 illustrates velocity reconstruction in accordance with one or more embodiments. Various embodiments of the present application consider an area or volume of interest as a 2D or 3D Doppler image with a single velocity component, $V_{Doppler}$, measured at every pixel or voxel, with some spatial location x which can be in Cartesian, Polar, or Spherical coordinates.

The component $V_{Doppler}$ is one of the terms for the velocity vector, which is written along with the unknown components U & W as $$\vec{u}(x) = (V_{Doppler}, U, W) \qquad \text{Equation 1}$$

In order to perform reconstruction, one must assume that the working fluid, whether Newtonian or Non-Newtonian, is incompressible. Therefore, the field must adhere to:

$$\nabla \cdot \vec{u}(x) = 0 \qquad \text{Equation 2}$$

The above assumption makes the velocity field divergence-free (solenoidal). One can now assume that each Doppler velocity component at every location is related to the unknown components by a scalar function, $\psi$, that still allows Equation 2 to be satisfied. This is the solenoidal flow condition, and $\psi$ is known as the streamfunction. Therefore $\psi$ relates to the velocity as $$\nabla \times \psi(x) = \vec{u}(x) \qquad \text{Equation 3}$$

One imposes an additional constraint based on the potential for the flow to rotate or shear, referred to as vorticity, $\omega$. Vorticity is defined as $$\nabla \times \vec{u}(x) = \omega(x) \qquad \text{Equation 4}$$

Rotation and shear are used in medical and meteorological applications, as they indicate the formation of vortical structures. By including and minimizing this constraint, we ensure that physical structures are not just consistent in appearance, but also in intensity. We may substitute Equation 2 into Equation 3 to obtain an elliptic equation that relates $\psi$ to $\omega$ $$\nabla^2 \psi(x) = \omega(x) \qquad \text{Equation 5}$$

The elliptic equation imposes a smoothness condition within the domain when solved and will converge to a suitable solution with minimal error so long as appropriate boundary conditions are provided. The above formulation holds for any orthogonal coordinate system but needs modifications when going from the 2D to the 3D formulation.

The algorithm for velocity reconstruction discussed in this application includes at least a single Doppler velocity field with a single velocity component (FIG. 2, 101), at each pixel or voxel location within the image. This data is pre-processed to assess if the data is in a single component format or provided in an RGB color image format. In the case of an image formation, a fast nearest-neighbor interpolation will be performed at each set of pixel or voxel values to convert it into their corresponding velocity based on the image color scale.

The user then provides or generates a "mask" region (FIG. 2, 102), corresponding to a domain for flow reconstruction using Equations 3, 4, and 5. The mask region will be the pixels or voxels over which Equation 4 is solved. User then specifies which "walls", or edges of the mask region are inlet or outlet for flow. Multiples of each condition may be selected. Specifying boundary classification is necessary for generating proper boundary conditions (FIG. 2, 103).

User also specifies a "starting point" along the boundary. This point will act as the streamfunction with initial value of zero and allow for physically consistent boundary conditions to be imposed. For each inlet and outlet, velocities normal to the boundary are integrated with the following equation:

$$\psi(\vec{x}) = \int_{x_0}^{x_1} \vec{u}(\vec{x^*}) d\xi + \psi_{Previous} \qquad \text{Equation 6}$$

Here, $\psi_{Previous}$ corresponds to the streamfunction value from the integral of the previous inlet or outlet that corresponded to the respective volume flow rate. Next, the walls are integrated, with the following forms:

$$\text{Moving } \psi(\vec{x}) = f(\vec{x}, \psi_{Previous})$$

$$\text{Stationary } \psi(\vec{x}) = \psi_{Previous} \qquad \text{Equation 7}$$

Once the domain is selected and proper boundary conditions are imposed for each image, one can solve for the missing velocity component(s) by solving Equation 5 for $\psi$ in an iterative sense with Equations 3 & 4 to obtain updated estimates of u and $\omega$(FIG. 2, 104). For each pass, Equation 5 is initialized with an estimate of vorticity from Equation 4. After initialization, Equation 5 is then solved with an elliptic PDE solver. Once complete, the original velocity values from the Doppler scan are placed back into the velocity field, and updated values for u and $\omega$ are obtained, after which the next iteration begins. This is done until the solution on $\psi$ does not change more than machine precision.

Figure 3:
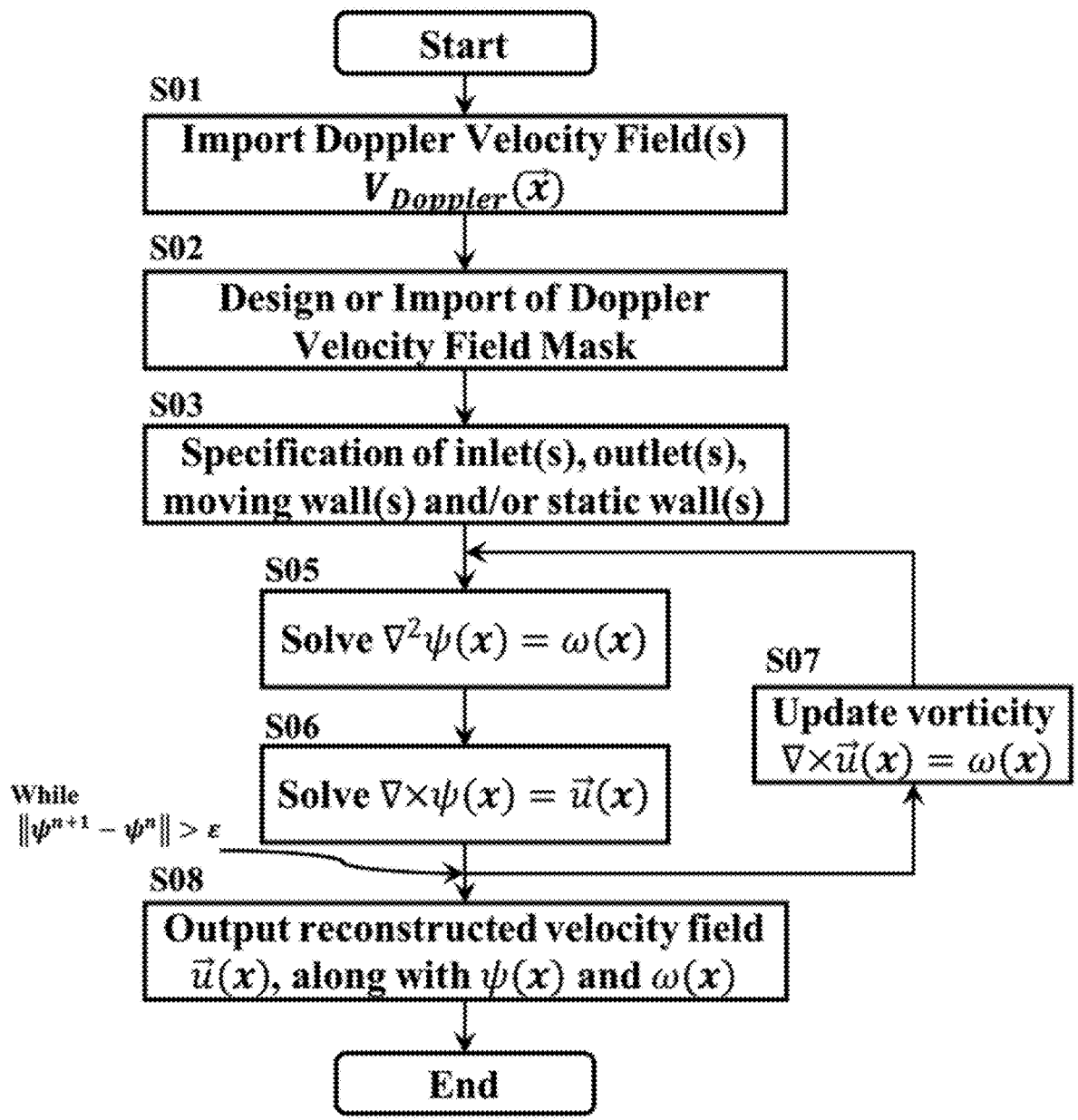
FIG. 3 illustrates an overview of an algorithm of processing an image in accordance with one or more embodiments.

User is then provided with an output that provides a 2-D, 2 component (FIG. 2, 105) or 3D-3C field of velocity estimates for each time point, streamfunction quantities for each time point that relate to flux, and vorticity quantities for each time point that relate to potential of rotation or shear. An overview of the algorithm work flow is provided in FIG. 3.

Figures 4, 5:
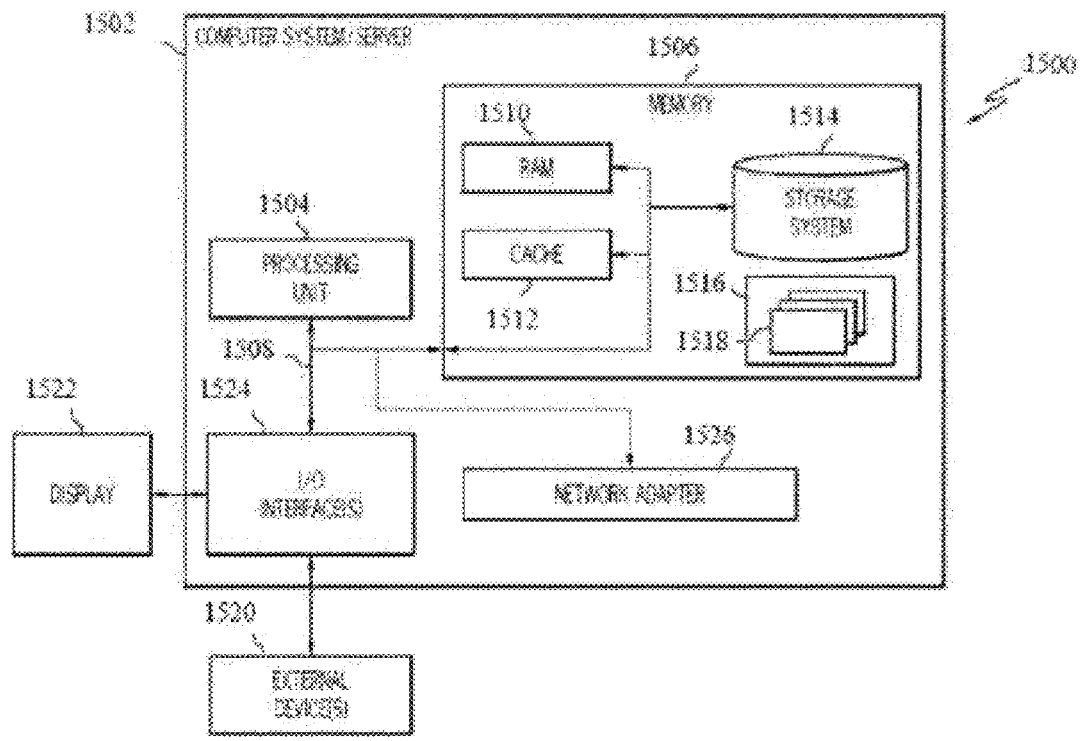
FIG. 4 illustrates a method of processing an image in accordance with one or more embodiments.
FIG. 5 illustrates one example of a computing or processing node 1500 for operating a method or a software architecture in accordance with the present application.

FIG. 4 illustrates a method of processing an image in accordance with one or more embodiments. Method 400 of processing an image starts off with step 405 of extracting a single component velocity field of a 2-D plane from a 2-D color Doppler image. Method 400 continues with step 410 of receiving a geometrical boundary of a region of interest within the 2-D color Doppler image. Method 400 additionally includes step 415 of applying a plurality of boundary conditions to the geometrical boundary, an at least one inlet, and an at least one outlet, of the single component velocity field of a 2-D plane. Additionally, method 400 includes step 420 of solving a streamfunction vorticity formulation to reconstruct a transverse velocity component based on the single component velocity field of a 2-D plane. Method 400 further includes step 425 of calculating a 2-D 2-component velocity field using the resulting streamfunction. Further, method 400 includes step 430 of reconstructing the transverse velocity component based on the 2-D 2-component velocity field. Next, method 400 includes step 430 of outputting a reconstructed 2-D 2-component velocity based on the transverse velocity component. Method 400 also includes step 435 of creating a velocity vector field image based on the reconstructed 2-D 2-component velocity. In some embodiments, the tolerance value is user defined. In some embodiments, the resulting streamfunction includes $\nabla \times \psi(x) = \vec{u}(x)$.

The solving the streamfunction includes initializing a plurality of vorticity values for each point of a flow field of the 2-D color Doppler image within the geometrical boundary of the region of interest. Additionally, the solving the streamfunction includes iterating, by solving numerically, Poisson Equation for the streamfunction with an iterated vorticity as a source term of the Poisson Equation until a difference between a resulting streamfunction and the streamfunction is below a tolerance value.

In various embodiments, method 400 additionally includes step 440 of characterizing the at least one inlet and the at least one outlet for the single component velocity field of a 2-D plane. In some embodiments, at least one of the at least one inlet or the at least one outlet is a moving wall for the single component velocity field of a 2-D plane. In some embodiments, at least one of the at least one inlet or the at least one outlet is a static wall for the single component velocity field of a 2-D plane.

In some embodiments, the applying the plurality of boundary conditions to the geometrical boundary includes defining the boundary conditions on the moving wall in terms of corresponding values of a streamfunction along or across the geometrical boundary of the 2-D color Doppler image. In some embodiments, the applying the plurality of boundary conditions to the geometrical boundary comprises defining the boundary conditions on the static wall in terms of corresponding values of a streamfunction along or across the geometrical boundary of the 2-D color Doppler image.

In at least one embodiment, the receiving the 2-D color Doppler image includes receiving a single 2-D color Doppler image. In some embodiments, the geometrical boundary is received through manual selection by a user. In some embodiments, the geometrical boundary is received through automatic segmentation of the 2-D color Doppler image. In some embodiments, the geometrical boundary is received through superimposition of a computer-aided design (CAD) image into the 2-D color Doppler image.

In one or more embodiments, the applying the plurality of boundary conditions to the geometrical boundary includes applying the plurality of boundary conditions that satisfy kinematic constraints of a flow field of the 2-D color Doppler image.

In one or more embodiments, the initializing the plurality of vorticity values for the each point of the flow field of the 2-D color Doppler image within the geometrical boundary of the region of interest includes performing a calculation denoted by $\nabla \times \vec{u}(x) = \omega 9x)$, wherein $\vec{u}(x)$ is the single component velocity field of a 2-D plane.

One of ordinary skill in the art would recognize that operations are added or removed from method 400, in one or more embodiments. One of ordinary skill in the art would also recognize that the order of the operations in method 400 is varied in various alternative embodiments.

Example 1

A software architecture encoded on a non-transitory computer readable medium, the software architecture includes a first protocol, wherein the first protocol is configured to receive a 2-D color Doppler image. The software architecture further includes a second protocol, wherein the second protocol is configured to extract a single component velocity field of a 2-D plane from the 2-D color Doppler image. Additionally, the software architecture includes a third protocol, wherein the third protocol is configured to receive a geometrical boundary of a region of interest within the 2-D color Doppler image. Further, the software architecture includes a fourth protocol, wherein the fourth protocol is configured to apply a plurality of boundary conditions to the geometrical boundary, an at least one inlet, and an at least one outlet, of the single component velocity field of a 2-D plane. Moreover, the software architecture includes a fifth protocol, wherein the fifth protocol is configured solving a streamfunction vorticity formulation to reconstruct a transverse velocity component based on the single component velocity field of a 2-D plane. The software architecture also includes a calculation protocol, wherein the calculation protocol is configured to calculate a 2-D 2-component velocity field using the resulting streamfunction. Moreover, the software architecture includes a reconstruction protocol, wherein the reconstruction protocol is configured to reconstruct the transverse velocity component based on the 2-D 2-component velocity field. Further, the software architecture includes a sixth protocol, wherein the sixth protocol is configured to output a reconstructed 2-D 2-component velocity based on the transverse velocity component. In some embodiments, the first protocol is configured to receive a single 2-D color Doppler image. In some embodiments, the tolerance value is user defined. In some embodiments, the resulting streamfunction includes $\nabla \times \psi(x) = \vec{u}(x)$.

The fifth protocol further includes a first module, wherein the first module is configured to initialize a plurality of vorticity values for each point of a flow field of the 2-D color Doppler image within the geometrical boundary of the region of interest. Additionally, the fifth protocol includes a second module, wherein the second module is configured to iterate, by solving numerically, Poisson Equation for the streamfunction with an iterated vorticity as a source term of the Poisson Equation until a difference between a resulting streamfunction and the streamfunction is below a tolerance value. In various embodiments, the first module comprises a third module, wherein the third module is configured to perform a calculation denoted by $\nabla \times \vec{u}(x) = \omega(x)$, wherein $\vec{u}(x)$ is the single component velocity field of a 2-D plane.

The software architecture additionally includes a seventh protocol, wherein the seventh protocol is configured to characterize the at least one inlet and the at least one outlet for the single component velocity field of a 2-D plane. In some embodiments, at least one of the at least one inlet or the at least one outlet is a moving wall for the single component velocity field of a 2-D plane. In some embodiments, at least one of the at least one inlet or the at least one outlet is a static wall for the single component velocity field of a 2-D plane.

In at least one embodiment, the fourth protocol includes an eighth protocol, wherein the eighth protocol is configured to define the boundary conditions on the moving wall in terms of corresponding values of a streamfunction along or across the geometrical boundary of the 2-D color Doppler image. In some embodiments, the fourth protocol includes a ninth protocol, wherein the ninth protocol is configured to define the boundary conditions on the static wall in terms of corresponding values of a streamfunction along or across the geometrical boundary of the 2-D color Doppler image.

In some embodiments, the third protocol is configured to receive the geometrical boundary through manual selection by a user. In some embodiments, the third protocol is configured to receive the geometrical boundary through automatic segmentation of the 2-D color Doppler image. In some embodiments, the third protocol is configured to receive the geometrical boundary through superimposition of a computer-aided design (CAD) image into the 2-D color Doppler image.

In one or more embodiments, the fourth protocol comprises a tenth protocol, wherein the tenth protocol is configured to apply the plurality of boundary conditions that satisfy kinematic constraints of a flow field of the 2-D color Doppler image.

FIG. 5 illustrates one example of a computing or processing node 1500 for operating the methods and the software architecture of the present application. This is not intended to suggest any limitation as to the scope of use or functionality of embodiments of the invention described herein. Regardless, the computing node 1500 is capable of being implemented and/or performing any of the functionality set forth hereinabove.

In computing node 1500 there is a computer system/server 1502, which is operational with numerous other general purpose or special purpose computing system environments or configurations. Examples of well-known computing systems, environments, and/or configurations that may be suitable for use with computer system/server 1502 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1502 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 502 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 1502 in cloud computing node 1500 is shown in the form of a general-purpose computing device. The components of computer system/server 1502 may include, but are not limited to, one or more processors or processing units 1504, a system memory 1506, and a bus 1508 that couples various system components including system memory 1506 to processor 1504.

Bus 1508 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1502 typically includes a variety of computer system readable media. Such media may be any available media that is accessible by computer system/server 1502, and it includes both volatile and non-volatile media, removable and non-removable media.

System memory 1506, in one embodiment, implements the methods and the software architectures of the present application. The system memory 506 can include computer system readable media in the form of volatile memory, such as random access memory (RAM) 1510 and/or cache memory 1512. Computer system/server 1502 may further include other removable/non-removable, volatile/non-volatile computer system storage media. By way of example only, storage system 1514 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1508 by one or more data media interfaces. As will be further depicted and described below, memory 1506 may include at least one program product having a set (e.g., at least one) of program modules that are configured to carry out the functions of various embodiments of the invention.

Program/utility 1516, having a set (at least one) of program modules 1518, may be stored in memory 1506 by way of example, and not limitation, as well as an operating system, one or more application programs, other program modules, and program data. Each of the operating system, one or more application programs, other program modules, and program data or some combination thereof, may include an implementation of a networking environment. Program modules 1518 generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Computer system/server 1502 may also communicate with one or more external devices 1520 such as a keyboard, a pointing device, a display 1522, etc.; one or more devices that enable a user to interact with computer system/server 1502; and/or any devices (e.g., network card, modem, etc.) that enable computer system/server 1502 to communicate with one or more other computing devices. Such communication can occur via I/O interfaces 1524. Still yet, computer system/server 1502 can communicate with one or more networks such as a local area network (LAN), a general wide area network (WAN), and/or a public network (e.g., the Internet) via network adapter 1526. As depicted, network adapter 1526 communicates with the other components of computer system/server 1502 via bus 1508. It should be understood that although not shown, other hardware and/or software components could be used in conjunction with computer system/server 1502. Examples, include, but are not limited to: microcode, device drivers, redundant processing units, external disk drive arrays, RAID systems, tape drives, and data archival storage systems, etc.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, design, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

The invention claimed is:

1. A non-transitory computer-readable medium encoded with a computer-readable program, which, when executed by a processor, will cause a computer to execute a method of processing an image, wherein the method comprises:
    extracting a single component velocity field of a 2-D plane from a 2-D color Doppler image;
    receiving a geometrical boundary of a region of interest within the 2-D color Doppler image;
    applying a plurality of boundary conditions to the geometrical boundary, an at least one inlet, and an at least one outlet, of the single component velocity field of a 2-D plane;
    solving a streamfunction vorticity formulation to reconstruct a transverse velocity component based on the single component velocity field of a 2-D plane, wherein the solving the streamfunction comprises:
        initializing a plurality of vorticity values for each point of a flow field of the 2-D color Doppler image within the geometrical boundary of the region of interest; and
        iterating, by solving numerically, Poisson Equation for the streamfunction with an iterated vorticity as a source term of the Poisson Equation until a difference between a resulting streamfunction and the streamfunction is below a tolerance value;
    calculating a 2-D 2-component velocity field using the resulting streamfunction;
    reconstructing the transverse velocity component based on the 2-D 2-component velocity field; and
    outputting a reconstructed 2-D 2-component velocity based on the transverse velocity component.

2. The method of claim 1, further comprising characterizing the at least one inlet and the at least one outlet for the single component velocity field of a 2-D plane.

3. The method of claim 2, wherein at least one of the at least one inlet or the at least one outlet is a moving wall for the single component velocity field of a 2-D plane.

4. The method of claim 2, wherein at least one of the at least one inlet or the at least one outlet is a static wall for the single component velocity field of a 2-D plane.

5. The method of claim 3, wherein applying the plurality of boundary conditions to the geometrical boundary comprises defining the boundary conditions on the moving wall in terms of corresponding values of a streamfunction along or across the geometrical boundary of the 2-D color Doppler image.

6. The method of claim 4, wherein applying the plurality of boundary conditions to the geometrical boundary comprises defining the boundary conditions on the static wall in terms of corresponding values of a streamfunction along or across the geometrical boundary of the 2-D color Doppler image.

7. The method of claim 1, wherein receiving the 2-D color Doppler image comprises receiving a single 2-D color Doppler image.

8. The method of claim 1, wherein receiving the geometrical boundary of the region of interest within the 2-D color Doppler image comprises receiving the geometrical boundary through manual selection by a user.

9. The method of claim 1, wherein receiving the geometrical boundary of the region of interest within the 2-D color Doppler image comprises receiving the geometrical boundary through automatic segmentation of the 2-D color Doppler image.

10. The method of claim 1, wherein receiving the geometrical boundary of the region of interest within the 2-D color Doppler image comprises receiving the geometrical boundary through superimposition of a computer-aided design (CAD) image into the 2-D color Doppler image.

11. The method of claim 1, wherein applying the plurality of boundary conditions to the geometrical boundary comprises applying the plurality of boundary conditions that satisfy kinematic constraints of a flow field of the 2-D color Doppler image.

12. The method of claim 1, wherein initializing the plurality of vorticity values for the each point of the flow field of the 2-D color Doppler image within the geometrical boundary of the region of interest comprises:

performing a calculation denoted by $\nabla \times \vec{u}(x) = \omega(x)$, wherein $\vec{u}(x)$ is the single component velocity field of a 2-D plane.

13. The method of claim 1, wherein the tolerance value is user defined.

14. The method of claim 1, wherein the resulting streamfunction comprises $\nabla \times \psi(x) = \vec{u}(x)$.

15. A non-transitory computer-readable medium encoded with a computer-readable program, which, when executed by a processor, will cause a computer to execute a method of processing an image, wherein the method comprises:

receiving a 2-D color Doppler image;
extracting a single component velocity field of a 2-D plane from the 2-D color Doppler image;
receiving a geometrical boundary of a region of interest within the 2-D color Doppler image;
applying a plurality of boundary conditions to the geometrical boundary, an at least one inlet, and an at least one outlet, of the single component velocity field of a 2-D plane;
solving a streamfunction vorticity formulation to reconstruct a transverse velocity component; and
outputting a reconstructed 2-D 2-component velocity based on the transverse velocity component,
wherein solving the streamfunction vorticity formulation to reconstruct the transverse velocity component comprises:
initializing a plurality of vorticity values for each point of a flow field of the 2-D color Doppler image within the geometrical boundary of the region of interest;
solving, numerically, Poisson Equation for the streamfunction with a vorticity as a source term of the Poisson Equation, thereby generating an updated streamfunction;
calculating a 2-D 2-component velocity field using the updated streamfunction; and
comparing the updated streamfunction with the streamfunction to determine whether a difference between the updated streamfunction and the streamfunction is above or below a tolerance value.

16. The method of claim 15, further comprising:
realizing the difference between the updated streamfunction and the streamfunction is above the tolerance value;
solving, numerically, the Poisson Equation for the streamfunction with a second vorticity as the source term of the Poisson Equation, thereby generating a second updated streamfunction;
calculating a second 2-D 2-component velocity field using the second updated streamfunction; and
comparing the second updated streamfunction with the streamfunction to determine whether a difference between the second updated streamfunction and the streamfunction is above or below the tolerance value.

17. The method of claim 15, further comprising reconstructing the transverse velocity component based on the 2-D 2-component velocity field, when the difference between the updated streamfunction and the streamfunction is below the tolerance value.

18. A non-transitory computer-readable medium encoded with a computer-readable program, which, when executed by a processor, will cause a computer to execute a method of processing an image, wherein the method comprises:

receiving a 2-D color Doppler image;
extracting a single component velocity field of a 2-D plane from the 2-D color Doppler image;
receiving a geometrical boundary of a region of interest within the 2-D color Doppler image;
applying a plurality of boundary conditions to the geometrical boundary, an at least one inlet, and an at least one outlet, of the single component velocity field of a 2-D plane;
solving a streamfunction vorticity formulation to reconstruct a transverse velocity component; and
outputting a reconstructed 2-D 2-component velocity based on the transverse velocity component.

19. The method of claim 18, wherein the solving the streamfunction comprises:
initializing a plurality of vorticity values for each point of a flow field of the 2-D color Doppler image within the geometrical boundary of the region of interest; and
iterating, by solving numerically, Poisson Equation for the streamfunction with an iterated vorticity as a source term of the Poisson Equation until a difference between a resulting streamfunction and the streamfunction is below a tolerance value.

20. The method of claim 19, further comprising:
calculating a 2-D 2-component velocity field using the resulting streamfunction; and
reconstructing the transverse velocity component based on the 2-D 2-component velocity field.

* * * * *